US010909129B2

(12) United States Patent
Sevenster et al.

(10) Patent No.: US 10,909,129 B2
(45) Date of Patent: Feb. 2, 2021

(54) AUTOMATED IDENTIFICATION OF SALIENT FINDING CODES IN STRUCTURED AND NARRATIVE REPORTS

(71) Applicant: KONINKLIJKE PHILIPS N.V., Eindhoven (NL)

(72) Inventors: Merlijn Sevenster, Haarlem (NL); Thomas Andre Forsberg, Hayward, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 147 days.

(21) Appl. No.: 16/315,179

(22) PCT Filed: Jul. 14, 2017

(86) PCT No.: PCT/EP2017/067944
§ 371 (c)(1),
(2) Date: Jan. 4, 2019

(87) PCT Pub. No.: WO2018/011426
PCT Pub. Date: Jan. 18, 2018

(65) Prior Publication Data
US 2019/0310981 A1 Oct. 10, 2019

Related U.S. Application Data

(60) Provisional application No. 62/362,767, filed on Jul. 15, 2016.

(51) Int. Cl.
*G06F 17/00* (2019.01)
*G06F 16/2458* (2019.01)
(Continued)

(52) U.S. Cl.
CPC ........ *G06F 16/2465* (2019.01); *G06F 40/284* (2020.01); *G06N 20/00* (2019.01);
(Continued)

(58) Field of Classification Search
CPC ... G06F 16/2465; G06F 40/284; G16H 10/60; G16H 50/20; G16H 15/00; G06N 20/00
See application file for complete search history.

(56) References Cited

U.S. PATENT DOCUMENTS

| 7,493,253 B1 | 2/2009 | Ceusters et al. |
| 7,917,377 B2 * | 3/2011 | Rao ..................... G06F 19/3481 705/3 |

(Continued)

OTHER PUBLICATIONS

Andrew MacKinlay and Karin Verspoor, Extracting Structured Information From Free-Text Medication Prescriptions Using Dependencies, In Proceedings of ACM Sixth International Workshop on Data and Text Mining Biomedical Informatics, pp. 35-40, Oct. (Year: 2012).*

(Continued)

*Primary Examiner* — Greta L Robinson

(57) ABSTRACT

In a tool for assisting in summarizing salient medical report findings, finding tokens (66) representing findings are extracted from a current medical report, and a salience value is computed for each such finding token based on statistics for the finding token in a reference database (32) including a count of reference medical reports of the containing the finding token in a report summary section and a count of reference medical reports containing the finding token anywhere in the report. A ranking or sub-set of findings extracted from the current medical report is displayed. The displayed findings may be ranked, or the sub-set chosen, by salience value. To generate the reference database, for each reference medical report (42) finding tokens (46) are extracted and it is determined whether each such finding token is salient based on whether the finding token is extracted from a report summary section of the reference report.

15 Claims, 3 Drawing Sheets

(51) Int. Cl.
*G16H 15/00* (2018.01)
*G06N 20/00* (2019.01)
*G16H 10/60* (2018.01)
*G16H 50/20* (2018.01)
*G06F 40/284* (2020.01)

(52) U.S. Cl.
CPC ............. *G16H 10/60* (2018.01); *G16H 15/00* (2018.01); *G16H 50/20* (2018.01)

(56) References Cited

U.S. PATENT DOCUMENTS

| | | | | |
|---|---|---|---|---|
| 8,473,452 | B1* | 6/2013 | Ober | G16H 20/00 707/607 |
| 2004/0243545 | A1* | 12/2004 | Boone | G06F 16/313 |
| 2008/0004505 | A1 | 1/2008 | Kapit et al. | |
| 2011/0033093 | A1 | 2/2011 | Salz et al. | |
| 2012/0278102 | A1 | 11/2012 | Johnson | |
| 2013/0046558 | A1* | 2/2013 | Landi | G16H 10/60 705/3 |
| 2014/0172456 | A1* | 6/2014 | Qian | G06F 16/248 705/3 |
| 2014/0297269 | A1 | 10/2014 | Qian et al. | |
| 2014/0343925 | A1 | 11/2014 | Mankovich et al. | |
| 2015/0095016 | A1 | 4/2015 | Karres et al. | |
| 2015/0294088 | A1 | 10/2015 | Walker et al. | |

OTHER PUBLICATIONS

David Martinez and Yue Li, Information Extraction from Pathology Reports in a Hospital Setting, In Proceedings of the 20th ACM International Conference on Information and Knowledge Management, Association for Computing Machinery, pp. 1877-1882, Oct. (Year: 2011).*

Byron C. Wallace, Joël Kuiper, Aakash Sharma, Mingxi Zhu, and Iain J. Marshall, Extracting PICO Sentences from Clinical Trial Reports using Supervised Distant Supervision, Journal of Machine Learning Research, vol. 17, issue 1, pp. 4572-4596, Jan. (Year: 2016).*

Vijayaraghavan Bashyam and Ricky K. Taira, Incorporating Syntactic Dependency Information Towards Improved Coding of Lengthy Medical Concepts in Clinical Reports, In Proceedings of the Workshop on Current Trends in Biomedical Natural Language Proc., Computational Linguistics, 125-132, Jun. (Year: 2009).*

* cited by examiner

AUTOMATED IDENTIFICATION OF SALIENT FINDING CODES IN STRUCTURED AND NARRATIVE REPORTS

CROSS-REFERENCE TO PRIOR APPLICATIONS

This application is the U.S. National Phase application under 35 U.S.C. § 371 of International Application No. PCT/EP2017/067944, filed on Jul. 14, 2017, which claims the benefit of U.S. Patent Application No. 62/362,767, filed on Jul. 15, 2016. These applications are hereby incorporated by reference herein.

FIELD

The following relates generally to the medical arts, and more particularly to medical reporting tools, electronic medical record (EMR) information systems, and the like.

BACKGROUND

Well-structured medical reports are crucial to record and disseminate medical findings obtained during medical examinations and procedures. Medical reports should be thorough in their description, and concise in presenting the findings. There are a vast amount of different medical reports depending on the medical domain, e.g. oncology, radiology, cardiology, and so forth. In the case of medical imaging, reports are furthermore distinguished between modalities (e.g. ultrasound, MRI etc.) and so on.

In one typical medical reporting scenario, a medical professional (e.g. a sonographer, cardiovascular sonographer, physician, or so forth) performs ultrasound imaging on a patient. The ultrasound machine is typically a mobile unit, e.g. on a cart or mounted on wheels, and is moved into the patient's hospital room to perform the examination. The findings of the echocardiogram or other ultrasound procedure are recorded in a medical report prepared by the medical professional. Preferably, this is done during or immediately after the ultrasound procedure, i.e. while the medical professional recalls the salient findings. Since the ultrasound machine is typically a heavily utilized medical instrument, the time frame for performing the ultrasound procedure and preparing the ultrasound examination report may be tight, e.g. on the order of a few tens of minutes or less.

In another typical medical reporting scenario, a radiologist performs readings of medical imaging sessions. The radiologist typically does not perform the imaging data acquisition personally; rather, the imaging session is performed by a medical technician or other specialist and the imaging data are stored in a Picture Archiving and Communication System (PACS). The radiologist then retrieves the images of the imaging session from the PACS, reviews the images to draw medical findings, and prepares a radiology report on those findings. As a highly trained and specialized medical professional, the radiologist is generally expected to handle a high workflow volume, and the radiologist may be expected to perform a complete reading of a medical imaging session on a time scale of a few minutes on average.

To facilitate rapid medical reporting, various tools may be employed. In some cases, the report may be dictated using voice recognition software, or dictation of the report may be recorded using a voice recorder and then transcribed by clerical staff. Additionally or alternatively, a structured report form may be used, optionally along with point-and-click or other rapid selection of "standard" finding codes representing commonplace findings. On the other hand, it is important to enable the medical professional to comprehensively express medical findings, which may be unique for, or specific to, a given patient. Accordingly, most medical reporting tools permit unstructured "narrative" entry of findings, e.g. as freeform text typed or dictated by the medical professional. Some medical reports may be mostly or entirely freeform text, without employing any structured report form or using a structured form only for basic patient data entry (e.g. name, age, gender, et cetera).

The completed medical report is distributed to "consumers" such as the patient's primary care physician and/or medical specialists. These medical professionals also often operate under tight time constraints. Accordingly, a common feature of medical reports is a report summary section (which may have some other titular name, e.g. a "Conclusion" section). The report summary is intended to aggregate and summarize the patient's condition and the most salient findings in a few key words or phrases. In practice, a busy medical professional with limited time availability may only review the report summary section, with reference to the main body of the report being made, if at all, only to clarify items in the summary.

Thus, the comprehensiveness of the report summary is of importance, since if a key finding is not in the summary it may be missed by a physician who relies on the summary in assessing the report findings. The reporting medical professional, operating under potentially tight time constraints, may fail to incorporate all salient findings of a report into the report summary, which could be detrimental to downstream patient care. This may occur due to inadvertent oversight, or due to a poor time-constrained decision as to whether a particular finding is sufficiently salient to include in the report summary. Salient findings are particularly likely to be omitted when the report is of narrative form, or includes a lengthy narrative portion. Another difficulty with preparing the report summary is that it is a time-consuming component of the overall medical report preparation process.

The following discloses new and improved systems and methods that address the above referenced issues, and others.

SUMMARY

In one disclosed aspect, a medical reporting device is disclosed. A training computer is programmed to perform a training process including, for each reference medical report of a reference database: (i) matching text of the reference medical report to finding templates of a set of finding templates to extract finding tokens representing findings from the reference medical report and (ii) determining whether each finding token extracted from the reference medical report is salient in the reference medical report. A report entry computer includes a display and one or more user interface devices. The report entry computer is programmed to receive user entry of a current medical report via the one or more user interface devices. The report entry computer is further programmed to perform a salient findings identification process including: (I) matching text of the current medical report to finding templates of the set of finding templates to extract finding tokens representing findings from the current medical report and (II) computing a salience value for each finding token extracted from the current medical report based on statistics generated by the training process including a count of reference medical reports from which the finding token was extracted and determined to be salient and a count of reference medical reports from which the finding token was extracted. The report entry computer is still further programmed to present, on the display, a sub-set or all findings extracted from the current medical report ranked by salience value.

In another disclosed aspect, a non-transitory storage medium stores instructions readable and executable by one or more computers to perform a medical reporting method. The method includes, for each reference medical report of a reference database: (i) extracting finding tokens representing findings from the reference medical report and (ii) determining whether each finding token extracted from the reference medical report is salient in the reference medical report based on whether the finding token is extracted from a report summary section. The method further includes extracting finding tokens representing findings from a current medical report and computing a salience value for each finding token extracted from the current medical report based on statistics for the finding token in the reference database including a count of reference medical reports from which the finding token was extracted and determined to be salient and a count of reference medical reports from which the finding token was extracted. The method further includes presenting, on a display, at least one of (1) all findings represented by finding tokens extracted from the current medical report ranked by salience value and (2) a sub-set of all findings represented by finding tokens extracted from the current medical report having highest salience value.

In another disclosed aspect, a medical reporting method comprises: extracting finding tokens representing findings from a current medical report; computing a salience value for each finding token extracted from the current medical report based on statistics for the finding token in a reference database including a count of reference medical reports of the reference database containing the finding token in a report summary section and a count of reference medical reports of the reference database containing the finding token anywhere in the reference medical report; and presenting, on a display, a ranking or sub-set of finding tokens extracted from the current medical report ranked, or the sub-set chosen, by salience value. The method may further include, for each reference medical report of the reference database: extracting finding tokens representing findings from the reference medical report; and determining whether each finding token extracted from the reference medical report is salient in the reference medical report by whether the finding token is extracted from a report summary section of the reference medical report.

One advantage resides in providing more comprehensive report summary sections.

Another advantage resides in providing reduced likelihood that a salient medical finding may be omitted from the report summary.

Another advantage resides in providing more efficient preparation of the report summary section.

Another advantage resides in providing guidance for identifying findings of sufficient saliency for inclusion in the report summary section.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention. Unless otherwise noted, the drawings are diagrammatic and are not to be construed as being to scale or to illustrate relative dimensions of different components.

DETAILED DESCRIPTION

Figure 1:
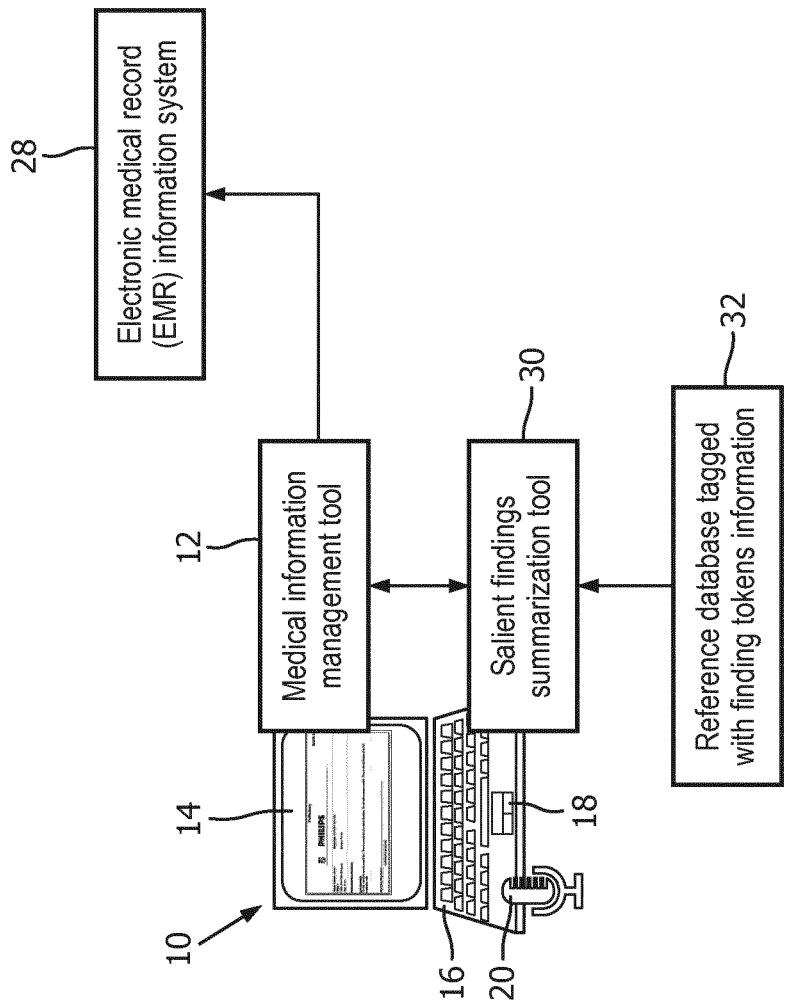
FIG. 1 diagrammatically shows a medical reporting tool for illustrative reporting of an echocardiogram examination.
Figure 1:
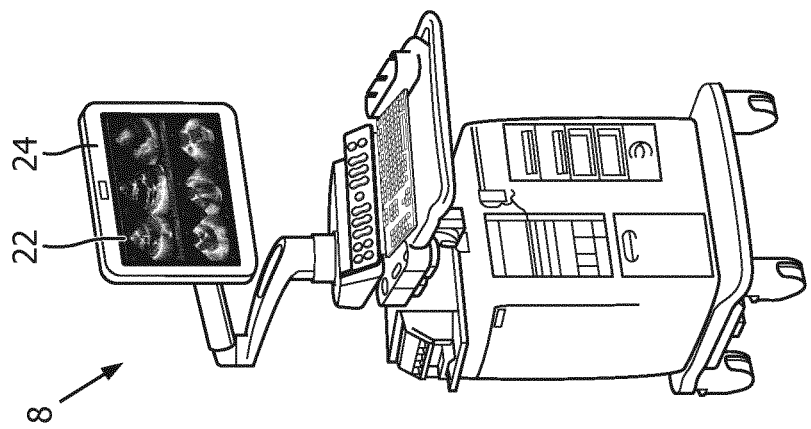

All findings of a medical report contribute to an overall view of a given examination or procedure; however, not all findings are equally relevant to the patient's medical condition. Findings carry different information content regarding the patient's medical condition. For instance, "This is a technically adequate echocardiographic examination" may be a finding that is commonly included in an echocardiography examination report—but it does not carry medical information or information directly related to the condition of the patient. The finding may nonetheless be included, as it is useful as contributing to a thorough description of the reported procedure—but it is not of high saliency so as to justify its inclusion in the report summary section.

The medical professional preparing the report makes professional judgments as to which findings included in the report should also be included in the report summary section. However, as noted previously the medical professional may unintentionally forget to include a salient finding in the summary section. Also, it is possible that a salient finding may be omitted from the summary section if the reporting medical professional does not appreciate the saliency of the finding.

In embodiments disclosed herein, the report author is given automated assistance in preparing the report summary section. (As previously noted, the report summary section may be known by other nomenclature such as a "conclusion" section, a "report synopsis" section, and any other nomenclature fitting within the spirit of a summary. The term "report summary section" as used herein is intended to encompass all such alternative nomenclature.) In some illustrative embodiments, "finding tokens" representing findings are extracted from the medical report. A "finding token" is a shorthand notation representing a finding, which is comparable across reports. In one approach, the text of the medical report is compared with finding templates of the set of finding templates to identify finding tokens. Each finding template comprises a set of semantic fields, with each semantic field being associated to a semantic category of a medical ontology. For example, a finding template may be (anatomy, diagnosis, severity) which is made up of the set of semantic fields "anatomy", "diagnosis", and "severity". If the report is a structured report (or contains a structured section) in which the user selects from standard finding codes of a set of standard finding codes, then the extraction of the finding token can be simplified to matching text of the medical report to standard finding codes of the set of standard finding codes.

The finding tokens introduce discretization to otherwise unstructured (e.g. natural language) report content, enabling statistical analysis of the report. After extracting the finding tokens from the report, a salience value is computed for each finding token. In one suitable embodiment, the salience value is computed based on statistics for the finding token in a reference database, for example including a count of reference medical reports of the reference database containing the finding token determined as salient in the reference report, and a count of reference medical reports of the reference database containing the finding token (regardless of whether it is a salient finding in the report). The more often the finding code is deemed salient in the reference reports database, the more likely that the finding code is salient in the current report. Optionally, the counts or other statistics of the reference database may be limited to reference medical reports having a predefined set of finding tokens also extracted from the current medical report, or having a predefined context, where the current medical report also has that predefined context. Such contextual or conditional statistics on saliency of a finding token can provide a more refined and accurate determination of whether the finding is likely to be salient in the currently entered report.

In some embodiments, no attempt is made to define a "salient" finding in terms of medical rationale. Rather, in one embodiment a finding token is deemed to be salient in a reference medical report if it is extracted from the report summary section; and is otherwise deemed to be not salient. Alternatively, salience of the various finding codes may be manually labeled, e.g. by a physician, for the reference reports of the reference database. This approach has the advantage of taking into account medical rationale, but at the cost of potentially laborious manual labeling of the findings in the reference reports.

Finally, the extracted findings are presented, e.g. on a display, for example as a ranking (or sub-set) of finding tokens extracted from the current medical report ranked (or the sub-set chosen) by salience value. Various user interfacing options can be employed for example, the ranking or sub-set of findings can be presented in a pop-up window or the like, and the report author can click on a finding (e.g. using a mouse) to select it for insertion into the report summary. If a sub-set of highest-salience findings is presented, then the sub-set may be chosen as a "top-N" sub-set in which a fixed number N of highest-salience findings are shown, or a threshold may be used, i.e. any finding whose salience value is above the threshold is included in the sub-set. In one illustrative embodiment, the selected finding is inserted into the report summary section by incorporating text of the current medical report representing the finding, optionally with some automated editing such as removal of verb phrases, articles, or other non-essential text. This advantageously uses the medical professional's own language for articulating the finding, which may capture nuances that might be lost using (for example) a standard expository text for the finding token.

With reference now to FIG. 1, in an illustrative example an echocardiographic examination of a patient (not shown) is performed using an ultrasound machine 8. The sonographer, cardiovascular sonographer, physician, or other medical professional who performs the echocardiographic examination preferably prepares a current medical report, here reporting on the echocardiography examination just performed using the ultrasound machine 8. To this end, a computer 10 (referred to herein as a report entry computer 10) is provided, which is programmed to implement a medical information management tool 12 having an echocardiogram report entry component (which may be more generally an ultrasound report entry component, or even more generally a medical report entry component). The computer 10 may, in general, be a notebook computer, a desktop computer (though this may not be preferable for use in conjunction with the portable ultrasound machine 8), a tablet computer, or so forth. In general, the computer 10 includes a display 14 and one or more user input devices, such as an illustrative keyboard 16, and/or an illustrative trackpad 18 or other pointing device (mouse, trackball, et cetera), and/or a microphone 20 for verbal dictation of the medical report. The medical information management tool 12 may, by way of non-limiting illustration, comprise a reporting environment such as the Xcelera Cardiology Information Management System or the IntelliSpace Cardiovascular Image and Information Management System (both available from Koninklijke Philips N.V., Eindhoven, the Netherlands). These are integrated multi-modality image management systems for cardiovascular information. Naturally, a different system may be chosen as the medical information management tool 12 depending upon the clinical area (e.g. oncology) and/or type of medical examination (e.g. hematology). The medical information management tool 12 provide an appropriate medical report entry environment (e.g., cardiovascular in the illustrative case of echocardiography examination) implemented on the report entry computer 10. In the illustrative echocardiography example, the medical professional preparing the report typically also performs the actual echocardiography data acquisition and accordingly may view echocardiogram images 22 on a display 24 of the ultrasound machine 8. In other reporting scenarios, the report entry component of the medical information management tool 12 may provide window(s) shown on the display 14 for displaying images under review (assuming some type of imaging examination). For example, in the case of a radiologist preparing a radiology report on a magnetic resonance (MR) or computed tomography (CT) imaging examination, the report entry component may include network connectivity for retrieving MR or CT images of the examination from a Picture Archiving and Communication System (PACS) and displaying selected MR or CT images for review by the radiologist. The current medical report prepared by the medical professional is suitably stored in an Electronic Medical Record (EMR) information system 28 or other medical data repository. In some cases, a radiology report may be stored on the PACS.

With continuing reference to FIG. 1, the report entry component of the medical information management tool 12 is augmented by a salient findings summarization tool 30 that extracts findings (e.g. represented as finding tokens as disclosed herein) from the medical report currently under preparation for possible inclusion in the report summary section of the medical report. Findings are identified by pattern matching (e.g. matching report text to a finding template) possibly augmented by natural language processing (NLP) to more precisely identify related words or phrases that collectively describe findings. Each extracted finding token is assessed as to saliency based on statistics on the finding token (including saliency statistics) obtained from a reference database 32 of reference medical reports which are tagged with finding tokens information (including saliency information).

Figure 2:
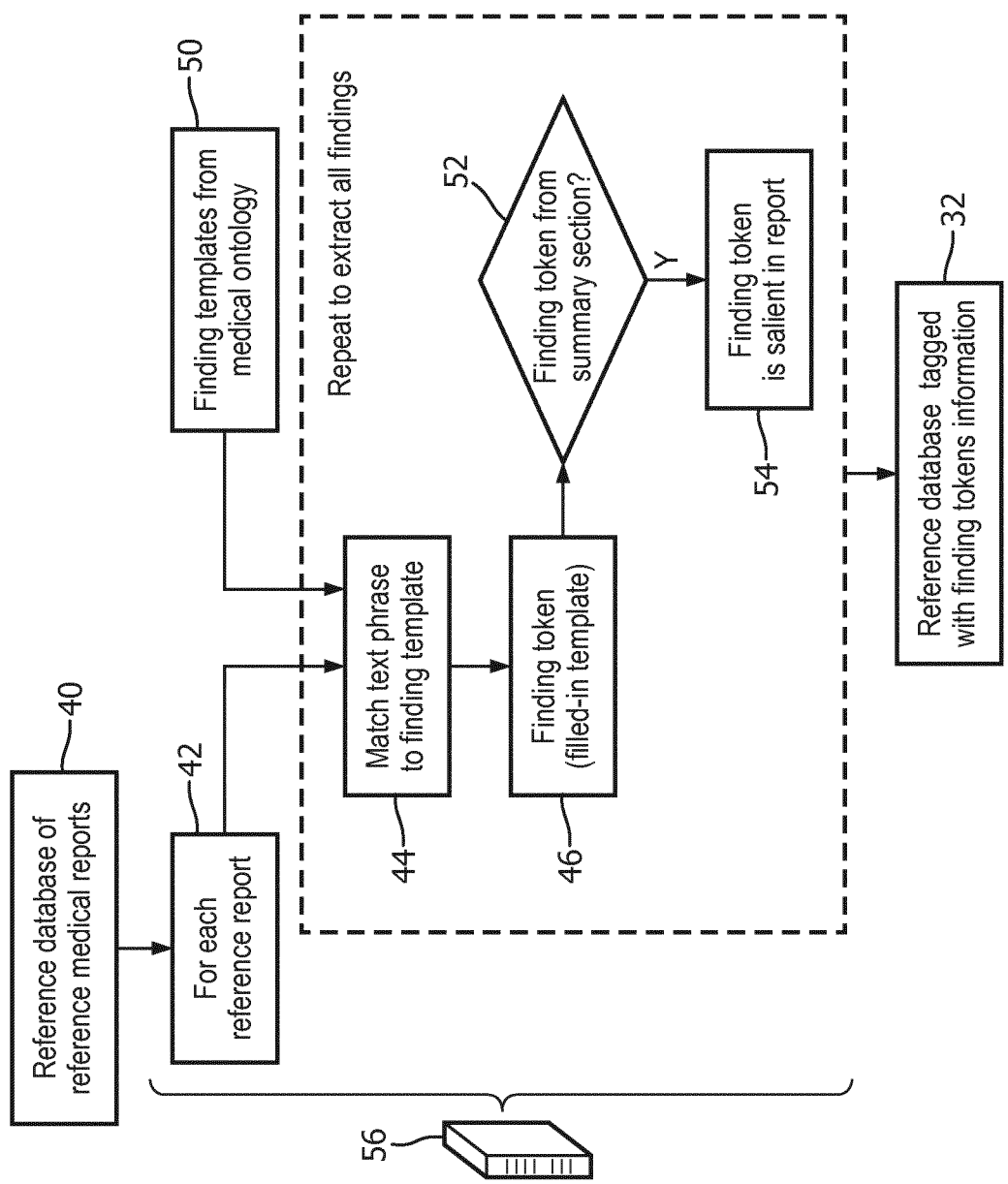
FIG. 2 diagrammatically shows a device for generating the reference database of FIG. 1 which is tagged with finding tokens information FIG. 3 diagrammatically shows the salient findings summarization tool of FIG. 1.

With reference now to FIG. 2, an approach for constructing the reference database 32 is described. The input is a reference database 40 of reference medical reports without tagged findings information. To add the findings information tagging, each reference medical report 42 is processed in turn. The text of the reference report 42 is processed in an operation 44 to extract finding tokens 46. In one approach, this is done by pattern matching of finding templates of a set of finding templates 50 constructed in accord with a suitable medical ontology, such as SNOMED and/or RadLex, and/or extracted concepts databases such as cTakes and/or MetaMap. A suitable processing approach is as follows. Sentence boundary detection is performed to determine the end of each sentence in free text, e.g. by searching for sentence transition sequences such as a period followed by a capitalized word. More complex rules and/or pattern matching techniques, and/or statistical algorithms, can also be used for identifying sentences and optionally other grammatical features, e.g. part-of-speech parsing. This is followed by concept extraction, in which phrases of text are extracted and normalized with respect to one or more medical ontologies, such as SNOMED or RadLex. Hierarchical reasoning may be applied to generalize the extracted concepts according to one or more semantic relationships defined in the medical ontology, such as "is-a". Using hierarchical reasoning, it can be derived if an extracted concept belongs to any of the semantic categories of the medical ontology that are used in the finding templates. Template filling (or matching) is next performed. In this step, semantic categories of extracted concepts are matched with template categories, in order to fill finding templates as appropriate. The completed template then forms a finding token, e.g. constructed by concatenating the individual concepts. The value of reducing a finding to a finding token is that the representation is generalized and standardized if two tokens are identical, then the underlying semantics of the text from which they were extracted should also be identical.

By way of illustration, the following illustrative example is presented. Using sentence boundary detection and optionally other natural language processing (NLP), the sentence "Left ventricle is moderately dilated" is isolated. The concepts "Left ventricle", "dilation" and "severe" are extracted from this sentence. Through hierarchical processing, the term "left ventricle" is associated with the anatomy category of the medical ontology. Similarly, the term "dilation" is associated with the diagnosis category, and the term "severe" is associated with a severity indicator category of the medical ontology. These terms extracted from the subject sentence are recognized as filling in the finding template (anatomy, diagnosis, severity) so as to create the finding token (left ventricle, dilatation, moderate"). This is merely an illustrative example. Table 1 summarizes these results.

In another contemplated implementation of the finding tokens extraction process 44, a finding token is obtained by grammatical analysis of parts of speech and related linguistic features such as word stems. In this approach, NLP processes such as grammatical parsing are applied recognize parts-of-speech (POS) in natural language content. By extracting nouns, adjectives and adverbs, or other grammatical parts, 2-tuple or 3-tuple tokens can be created, and correspondences of such tuples with a natural language string (i.e. token template) are identified, e.g. "Left ventricle is moderately dilated" can be reduced to [Left ventricle, moderately, dilated] or [Left ventricle, dilated]. Stemming may also be applied. By stemming sentences to account for lexical variations, removing stop words, and sorting the remaining words in alphabetical order, sentences are itemized in such a way that they are comparable to each other (i.e. countable), e.g. "Left ventricle is moderately dilated" can be transformed to "dilat left moder ventricle". This approach has the advantage of fitting all sentence structures, as opposed to the POS-tagging implementation.

TABLE 1

Finding token for the text "Left ventricle is moderately dilated"

| | Finding template field | | |
|---|---|---|---|
| | Anatomy | diagnosis | severity |
| Value | ventricle | dilat left | moder |

In another contemplated implementation of the finding tokens extraction process 44, words or phrases of a medical ontology are extracted from the reference medical report 42. Combinations of the extracted words or phrases matching finding templates of the set of finding templates 50 are identified to extract the finding tokens 46 representing findings from the reference medical report 42. This approach does not rely upon POS tagging or NLP. The allowable combinations of ontology words or phrases may be limited to some maximum permissible separation, e.g. if two ontology words or phrases are separated by more than a specified maximum number of intervening words then they cannot be identified as a combination for matching to a finding template.

As yet another example of a suitable implementation of the finding tokens extraction process 44, the report entry component may enable user entry of at least a portion of the medical report by filling in a structured medical report form, including user selection of standard finding codes of a set of standard finding codes. For example, the Xcelera Cardiology Information Management System provides for retrieving standard finding codes using appropriate Application Program Interface (API) components. In this case, the finding tokens extraction process 44 can be implemented by matching text of the reference medical report to standard finding codes of the set of standard finding codes.

The output of the operation 44 is the set of finding tokens annotated (i.e. tagged) to the reference medical report 42. Additionally, in a decision operation 52 it is determined whether each finding token is salient in the reference report 42. In a suitable approach, a finding token is determined to be salient 54 if it is included in the report summary section of the reference report 42; otherwise, the finding token is determined to be not salient. To efficiently make this assessment, the token extraction process 44 may be applied first to the report summary section of the reference report 42, and any finding tokens extracted from the summary section are determined in the operation 52 to be salient 54. Thereafter, the remainder of the reference report is processed by the token extraction process 44, and any additional finding tokens that are found that were not (also) extracted from the summary section are then determined to be not salient.

As previously noted, the processing 44, 52 is repeated to identify all finding tokens in the reference report 42, and the finding tokens (from process 44) and their saliency (from determination 52) are tagged to the reference report 42. This is then repeated for every reference medical report in the reference database 40, thereby generating the reference database 32 in which the reference medical reports are each tagged with finding tokens information (including saliency data). It may be noted that this processing may be extensive if the reference database 40 contains many reference medical reports, which is preferably the case in order to generate a large statistical database for assessing finding saliency. In view of the computational complexity of this training process, it is optionally performed by a computer 56 that is of higher computational capacity than the report entry computer 10 of FIG. 1 which processes only a single (current)

medical report at any given time. The higher-capacity computer 56 may, for example, be a network server computer or a computing resource such as a cluster computer, cloud computing resource, or the like. Alternatively, it is contemplated for the single computer 10 to perform both the report entry functionality (including the salient findings summarization tool 30) and the training of FIG. 2.

Figure 3:
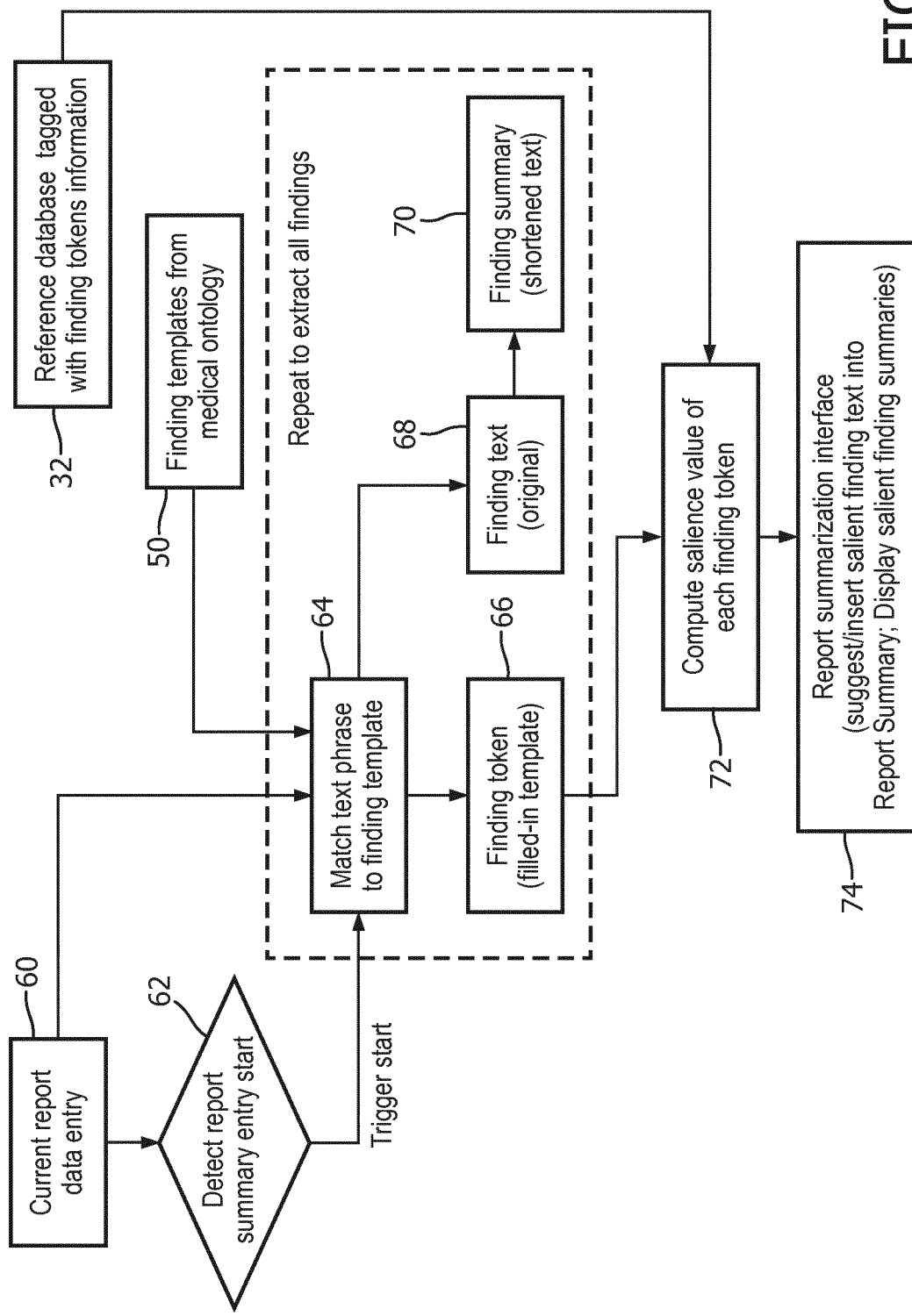

With reference now to FIG. 3, an illustrative implementation of the salient findings summarization tool 30 is described, which makes use of the reference database 32 including finding tokens/saliency tagging generated by the training system of FIG. 2. In general, the medical professional is authoring the current medical report in current report data entry operation 60, e.g. performed using the report entry component of the medical information management tool 12 (see FIG. 1). The salient findings summarization tool 30 is invoked by a detection operation 62 that detects the start of entry of the report summary section. The operation 62 can take various forms, such as detecting placement of the text entry cursor into the report summary section of a (at least semi-structured) report form. In another approach, the operation 62 is implemented by modifying the report entry component to include a control (e.g. clickable button) that can be selected by the user during entry of the current medical report in order to manually invoke the salient findings summarization tool 30. In an unstructured report entry environment, the operation 62 is contemplated to entail text entry by the user of a standard heading for the report summary section, such as detecting typing of the word "Conclusion" or "Summary".

The detection operation 62 triggers start of execution of the salient findings summarization tool 30. The processing includes applying a finding tokens extraction process 64 to the medical report currently being entered in order to extract finding tokens representing findings contained in the current medical report. The finding tokens extraction process 64 can, in some embodiments, be similar to, or identical with, the finding tokens extraction process 44 already described with reference to FIG. 2, except that the finding tokens extraction process 64 is applied to the current medical report rather than to a reference medical report 42. However, some differences between the two extraction processes 44, 64 are contemplated. For example, since a goal of the reference medical reports tagging process of FIG. 2 is to identify salient finding codes as those present in the summary section, the extraction process 44 may start with processing of the reference report summary section so as to efficiently identify the finding tokens in the summary section. By contrast, since the goal of the finding tokens extraction process 64 is to extract findings from the body of the current report for possible inclusion in the summary section, the finding tokens extraction process 64 optionally is not applied to the summary section at all. (In any event, the summary section of the current report is typically not yet completed, and may not yet even have been started, when the salient findings summarization tool 30 is invoked by the detection operation 62).

Like the finding tokens extraction process 44 of FIG. 2, the output of the finding tokens extraction process 64 is a set of finding tokens 66, but here extracted from the medical report currently being entered. Additionally, since it is preferable for the report summary to articulate findings in a manner similar or identical to the articulation entered by the medical professional in the body of the current medical report, the original finding text 68 may optionally also be extracted. Additionally or alternatively, the original finding text 68 may be pre-processed to provide a shorter version 70 of the finding articulation that may be more convenient for the summary section. For example, the finding summary 70 may be generated from the original finding text 68 by removing non-essential substrings, for instance, by removing verb phrases, articles, et cetera. This enables easier reading of the principal findings in the report summary.

In addition to extracting the finding tokens representing the findings contained in the current medical report, the salient findings summarization tool 30 also performs an operation 72 in which a salience value is computed for each finding token extracted from the current medical report. The salience value is suitably computed based on statistics generated by the training process of FIG. 2. These statistics may include, for example, a count of reference medical reports from which the finding token was extracted and determined to be salient, and a count of reference medical reports from which the finding token was extracted. The detailed computation of the salience value can be variously formulated. In the following examples, the salience of a finding represented by a finding token A is denoted as S(A).

In one embodiment, the salience S(A) of a finding token A is given by:

$$S(A) = \frac{\text{\# reference reports with } A \text{ being salient}}{\text{\# reference reports with } A} \quad (1)$$

In Equation (1), the numerator (# reference reports with A being salient) is suitably generated as a count of the results of operations 52, 54 of the training process of FIG. 2 (e.g. counting only those reference reports in which finding code A is extracted from the reference report summary). The denominator (# reference reports with A) is suitably generated as a count of the results of operations 44, 46 of the training process of FIG. 2 (i.e. counting all reference reports containing the finding code A anywhere in the report).

The salience value produced by Equation (1) is straightforward to calculate; however, it does not consider the context in which the finding A is made. In another embodiment, the salience of a finding token A is calculated taking into account a context of the finding A being made in combination with some other finding or findings:

$$S(A \mid B, C) = \frac{\text{\# reference reports with } A, B, \text{ and } C \text{ and with } A \text{ being salient}}{\text{\# reports with } A, B, \text{ and } C} \quad (2)$$

where in this illustrative example of Equation (2) the context is the finding A being made in combination with two other findings B and C. The illustrative salience value S(A) of Equation (2) can be readily generalized to a context comprising an arbitrary numbers of other findings, e.g. one other finding, two other findings (as in Equation (2)), three other findings, or more other findings.

The definition of the context can be extended to other features of the medical report beside a combination of findings. These other features may be suitably represented as a context vectors v that codifies the chosen contextual parameters of the report. By way of non-limiting example, these contextual features may include various combinations of features such as type of imaging modality (for imaging examination reports), patient demographic features such as gender and/or age cohort, prior medical history, patient characteristics such as being a smoker, contents of prior reports and so on. With the contextual features encoded as the context vector v the expression for the salience value can be written as:

$$S(A \mid v) = \frac{\text{\# reference reports with context } v \text{ and with } A \text{ being salient}}{\text{\# reference reports with context } v \text{ and with } A} \quad (3)$$

The context may include both a chosen one or more other findings (e.g. B,C) and a context vector v, yielding the salience value:

$$S(A \mid B, C, v) = \frac{\text{\# reference reports with context } v \text{ and with } A, B, \text{ and } C \text{ with } A \text{ being salient}}{\text{\# reference reports with context } v \text{ and with } A, B \text{ and } C} \quad (4)$$

The foregoing are merely illustrative salience value calculations, and other formulations are contemplated for computing a salience value for a finding token extracted from the current medical report based on statistics generated by the training process of FIG. 2 including a count of reference medical reports from which the finding token was extracted and determined to be salient and a count of reference medical reports from which the finding token was extracted. For example, the salience value may is computed as an information gain quantified through (conditional) entropy. The illustrative salience value calculations of Equations (1)-(4) each yield a salience value in the range [0,1] with a salience value of 0 indicating minimal salience (e.g. no reference report listing the finding code A in its report summary section) and a salience value of 1 indicating maximal salience (e.g. every reference report containing the finding token including it in its report summary section).

In embodiments in which salience value is computed based on statistics of counts of reports with the finding and of reports with the finding in the summary section, the salience is effectively defined by the statistics of clinicians' judgement as to salience as reflected by their statistical decisions on whether to include the finding in the report summary section. This approach advantageously makes no assumptions regarding what is salient to a given clinician or medical institution, but rather leverages existing empirical data in the form of the reference database 40 used in the training phase of FIG. 2.

With continuing reference to FIG. 3, in an operation 74 a report summarization interface is provided via which the salient findings are presented to the user. This may be done in various ways, such as presenting a ranking or sub-set of findings in a pop-up window or other display area shown on the display 14 (see FIG. 1). In one approach, the report author can click on a finding (e.g. using the trackpad 18) to select it for insertion into the report summary of the medical report currently being entered. In one illustrative embodiment, the selected finding is inserted into the report summary section by incorporating the original text 68 of the current medical report representing the finding, or by inserting into the report summary the shortened finding text 70 in which automated editing has removed verb phrases, articles, or other non-essential text.

The illustrative implementation of the salient findings summarization tool 30 shown in FIG. 3 is suitably executed on the report entry computer 10 of FIG. 1. In some embodiments, the summarization interface 74 may be integrated with the report entry component of the medical information management tool 12, e.g. the interface 74 may be implemented as a plug-in of the medical information management tool 12. It will also be appreciated that the processing described with illustrative reference to FIGS. 2 and 3 may be implemented as a non-transitory storage medium storing instructions readable and executable by one or more computers 10, 56 to perform the disclosed operations. Various levels of integration of componentization of the various elements are also contemplated. For example, in illustrative FIG. 1 the ultrasound machine 8 performs the ultrasound examination while the separate report entry computer 10 provides the user interfacing for entering the medical (e.g. ultrasound examination) report. However, in a variant embodiment, the ultrasound machine may integrally include a report entry component, thereby integrating the components 8, 10. On the other hand, in the case of a radiology reporting scenario, the radiology report entry may be performed using a radiology workstation that is located in a different room from the imaging data acquisition equipment (indeed, the radiology workstation may be located in a different building from the imaging system).

The training process of FIG. 2 may optionally be repeated occasionally to ensure the tagged reference database 32 reflects up-to-date statistical clinical assessment of the saliency of various findings. In some embodiments, such updating is performed in batch mode, i.e. the entire process of FIG. 2 is repeated. In other embodiments, such updating may be performed on a rolling basis, e.g. more recent reference reports may be processed and added to the database 32, while the oldest reference reports in the database 32 (based on the report date) are removed.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical reporting device comprising:
    a training computer programmed to perform a training process including, for each reference medical report of a reference database (i) matching text of the reference medical report to finding templates of a set of finding templates to extract finding tokens representing findings from the reference medical report and (ii) determining whether each finding token extracted from the reference medical report is salient in the reference medical report; and
    a report entry computer including a display and one or more user interface devices, the report entry computer programmed to:
        receive user entry of a current medical report via the one or more user interface devices and at least a portion of the current medical report by filling in a structured medical report form is user selection via the one or more user interface devices of standard finding codes of a set of standard codes;
        perform a salient findings identification process including: (I) matching text of the current medical report to finding templates of the set of finding templates to extract finding tokens representing findings from the current medical report and matching text of the current medical report to standard finding codes of the set of standard finding codes and (II) computing a salience value for each finding token extracted from the current medical report based on statistics generated by the training process including a count of reference medical reports from which the finding token was extracted and determined to be salient and a count of reference medical reports from which the finding token was extracted; and present, on the display, a sub-set or all findings extracted from the current medical report ranked by salience value.

2. The medical reporting device of claim 1 wherein the operation (ii) comprises:

determining whether each finding token extracted from a report summary section of the reference medical report is salient in the reference medical report, the finding token being not salient otherwise.

3. The medical reporting device of claim 1 wherein the operation (ii) comprises:

receiving from a user an indication of whether each finding token extracted from the reference medical report is salient in the reference medical report.

4. The medical reporting device of claim 1 wherein each finding template of the set of finding templates comprises a set of semantic fields wherein each semantic field is associated to a semantic category of a medical ontology.

5. The medical reporting device of claim 4 wherein semantic fields of the finding templates of the set of finding templates include at least: a semantic field associated to an anatomy category of the medical ontology; a semantic field associated to a diagnosis category of the medical ontology; and a semantic field associated to a severity category of the medical ontology.

6. The medical reporting device of claim 1 wherein the matching operations (i) and (I) comprise:

extracting words or phrases of a medical ontology from the reference or current medical report; and identifying combinations of the extracted words or phrases matching finding templates of the set of finding templates to extract finding tokens representing findings from the reference or current medical report.

7. The medical reporting device of claim 1 wherein, in the operation (II), the counts are limited to reference medical reports having a predefined set of finding tokens also extracted from the current medical report.

8. The medical reporting device of claim 1 wherein, in the operation (II), the counts are limited to reference medical reports having a predefined context, the current medical report also having the predefined context.

9. The medical reporting device of 1 wherein the report entry computer is programmed to present said sub-set or all findings by presenting text of the current medical report representing each finding.

10. The medical reporting device of claim 1 wherein the training computer and the report entry computer are a single computer.

11. A non-transitory storage medium storing instructions readable and executable by one or more computers to perform a medical reporting method comprising:

receive user entry of a current medical report via one or more user interface devices and at least a portion of the current medical report in a structured medical report form including user selection via the one or more user interface devices of standard finding codes of a set of standard finding codes:

for each reference medical report of a reference database: (i) extracting finding tokens representing findings from the reference medical report and (ii) determining whether each finding token extracted from the reference medical report is salient in the reference medical report based on whether the finding token is extracted from a report summary section;

extracting finding tokens representing findings from a current medical report;

computing a salience value for each finding token extracted from the current medical report based on statistics for the finding token in the reference database including a count of reference medical reports from which the finding token was extracted and determined to be salient and a count of reference medical reports from which the finding token was extracted; and presenting, on a display, at least one of all findings represented by finding tokens extracted from the current medical report ranked by salience value and a sub-set of all findings represented by finding tokens extracted from the current medical report having highest salience value.

12. The non-transitory storage medium of claim 11 wherein the extracting of finding tokens from the reference or current medical report includes:

extracting words or phrases of a medical ontology from the reference or current medical report; and identifying combinations of the extracted words or phrases matching finding templates of a set of finding templates wherein the identified combinations form the finding tokens representing findings from the reference or current medical report.

13. The non-transitory storage medium of claim 11 wherein the counts are limited to reference medical reports having a predefined set of finding tokens which are also extracted from the current medical report.

14. The non-transitory storage medium of claim 11 wherein the counts are limited to reference medical reports having a predefined context, the current medical report also having the predefined context.

15. The non-transitory storage medium of claim 11 wherein the presenting includes presenting said all findings or said sub-set of all findings by presenting text of the current medical report representing each finding.

* * * * *